United States Patent
Choi

(10) Patent No.: US 9,102,066 B2
(45) Date of Patent: Aug. 11, 2015

(54) ROBOTIC SHOE

(71) Applicant: Hyundai Motor Company, Seoul (KR)

(72) Inventor: Jae Young Choi, Yongin-si (KR)

(73) Assignee: HYUNDAI MOTOR COMPANY, Seoul (KR)

( * ) Notice: Subject to any disclaimer, the term of this patent is extended or adjusted under 35 U.S.C. 154(b) by 158 days.

(21) Appl. No.: 13/861,059

(22) Filed: Apr. 11, 2013

(65) Prior Publication Data

US 2014/0188278 A1  Jul. 3, 2014

(30) Foreign Application Priority Data

Dec. 27, 2012  (KR) .................. 10-2012-0154470

(51) Int. Cl.
*B25J 19/02* (2006.01)
*A43B 3/00* (2006.01)
*A61B 5/103* (2006.01)
*B62D 57/032* (2006.01)

(52) U.S. Cl.
CPC ............. *B25J 19/021* (2013.01); *A43B 3/0005* (2013.01); *A61B 5/1036* (2013.01); *B62D 57/032* (2013.01); *A63B 2220/56* (2013.01)

(58) Field of Classification Search
None
See application file for complete search history.

(56) References Cited

U.S. PATENT DOCUMENTS

| | | | | |
|---|---|---|---|---|
| 4,703,445 A | * | 10/1987 | Dassler | 702/160 |
| 4,814,661 A | * | 3/1989 | Ratzlaff et al. | 310/328 |
| 5,500,635 A | * | 3/1996 | Mott | 340/323 R |
| 6,058,627 A | * | 5/2000 | Violette et al. | 36/61 |
| 7,156,773 B2 | * | 1/2007 | Takai et al. | 482/7 |
| 7,171,331 B2 | * | 1/2007 | Vock et al. | 702/160 |
| 7,426,873 B1 | * | 9/2008 | Kholwadwala et al. | 73/818 |
| 7,676,960 B2 | * | 3/2010 | DiBenedetto et al. | 36/132 |
| 8,011,229 B2 | * | 9/2011 | Lieberman et al. | 73/65.01 |
| 8,739,639 B2 | * | 6/2014 | Owings et al. | 73/862.046 |
| 8,957,785 B1 | * | 2/2015 | Matak et al. | 340/870.07 |
| 2005/0233859 A1 | * | 10/2005 | Takai et al. | 482/3 |
| 2009/0107009 A1 | * | 4/2009 | Bishop et al. | 36/114 |
| 2009/0109659 A1 | * | 4/2009 | Harris | 362/103 |
| 2009/0260426 A1 | * | 10/2009 | Lieberman et al. | 73/65.01 |
| 2011/0301504 A1 | * | 12/2011 | Lan et al. | 600/592 |
| 2012/0253234 A1 | * | 10/2012 | Yang et al. | 600/595 |

FOREIGN PATENT DOCUMENTS

| | | |
|---|---|---|
| EP | 1637050 A1 | 3/2006 |
| JP | H07-284403 A | 10/1995 |
| JP | 2003-181781 A | 7/2003 |
| JP | 2010-509000 A | 3/2010 |
| KR | 10-0920224 B1 | 10/2009 |
| KR | 10-2009-0122595 A | 12/2009 |
| KR | 10-2010-0003207 A | 1/2010 |
| KR | 10-2011-0076418 A | 7/2011 |
| KR | 10-1179159 B1 | 9/2012 |
| WO | 2008/061023 A2 | 5/2008 |

* cited by examiner

*Primary Examiner* — Jason Holloway
(74) *Attorney, Agent, or Firm* — McDermott Will & Emery LLP

(57) ABSTRACT

A robotic shoe includes a robot sole, a plurality of optical sensors, and projections. The robot sole has an underside capable of contacting the ground when in use. Mounting spaces are longitudinally spaced in the sole. The optical sensors are disposed in respective ones of the mounting spaces. The projections protrude from the underside of the sole, and are capable of contacting the ground at positions corresponding to the mounting spaces.

7 Claims, 4 Drawing Sheets

ROBOTIC SHOE

CROSS-REFERENCE TO RELATED APPLICATION

This application is based on and claims benefit of priority to Korean Patent Application No. 10-2012-0154470, filed on Dec. 27, 2012 in the Korean Intellectual Property Office, the entire contents of which are hereby incorporated by reference.

TECHNICAL FIELD

The present inventive concept relates to a robotic shoe capable of recognizing a walking pattern, when a force enhancement wearable robot or a humanoid robot walks.

BACKGROUND

Many studies of wearable robots enhancing muscular power on a human body or humanoid robots have been conducted with development of the technology about robots. Sensors are mounted on the soles of the feet to be able to recognize walking patterns when wearable robots or humanoid robots are walking.

According to KR10-2010-0003207 A, titled "Foot sensor apparatus for wearable robot and method for determining intention of user using the same", particularly a pressure sensor in a plurality of contact type sensors is mounted on a foot of a robot, so that when the sensor is operated by pressure of the sole on the ground, the intention of a walker is determined.

FIG. 1 is a view of a robotic shoe of the related art. The sole is composed of an upper part and a lower part. The lower part is made of an elastic material, so the lower part can sensitively respond to a change in pressure.

FIG. 2 is a view when the robotic shoe of the related art is not in contact with the ground G, showing that pressure is not applied to a pressure sensor 50 mounted on a sole 10. In general, the pressure sensor 50 uses a tape switch that is a contact type sensor. FIG. 3 is a view showing the robotic shoe in contact with the ground G. As shown in FIG. 3, when the underside of the sole 10 comes in contact with the ground G, the bottom is pushed up inside a mounting space 30 by pressure and the pressure is applied to the pressure sensor 50. Therefore, the pressure sensor 50 operates and the sensed information is transmitted to a controller 90 (see FIG. 1), thereby determining the intention of walking.

However, it is required that the contact type sensor should operate even with small pressure and have durability that can resist considerable load. The durability and reliability of the sensor are likely to be decreased by repetitive load.

Therefore, there is a need to develop a robotic shoe that can resist a considerable load while sensitively responding to an ever-changing environment, that maintains durability and reliability of sensors even under repetitive loads.

The description provided above is just for helping understanding the background of the present inventive concept and should not be construed as being included in the related art known by those skilled in the art.

PRIOR ART DOCUMENT

Patent Document (Patent Document 1) KR10-2010-0003207 A

SUMMARY

The present inventive concept has been made in an effort to solve the problems and an object of the present inventive concept is to provide a robotic shoe that can resist considerable load while sensitively responding to an ever-changing environment and maintain durability and reliability of sensors even under repetitive load.

One aspect of the present inventive concept encompasses a robotic shoe including a robot sole having an underside capable of contacting the ground when in use, a plurality of mounting spaces longitudinally spaced in the sole, a plurality of optical sensors disposed in respective ones of the mounting spaces, and projections protruding from the underside of the sole, which are capable of contacting the ground when in use at positions corresponding to the mounting spaces.

The mounting spaces may be formed along a width direction of the sole.

The optical sensors may be disposed on a top portion of the mounting spaces and configured to radiate light downward from above.

The optical sensors may be configured to sense distances from the optical sensors to bottom portions of the mounting spaces and operate when a sensed distance value is equal to or less than a predetermined value.

The robotic shoe may further include a controller configured to determine an intention of walking on the basis of the order of sensed signals of the optical sensors.

The optical sensors may be non-contact type photosensors.

When the projections come in contact with the ground, bottom portions of the mounting spaces may be pushed into the mounting spaces and a distance between the optical sensors and the bottom portions of the mounting spaces may be decreased.

The portions of the sole where the mounting spaces are formed in the sole may be made of an elastic material.

BRIEF DESCRIPTION OF THE DRAWINGS

The above and other features of the present inventive concept will now be described in detail with reference to certain exemplary embodiments thereof illustrated the accompanying drawings which are given hereinbelow by way of illustration only, and thus are not limitative of the present invention.

Figure 1:
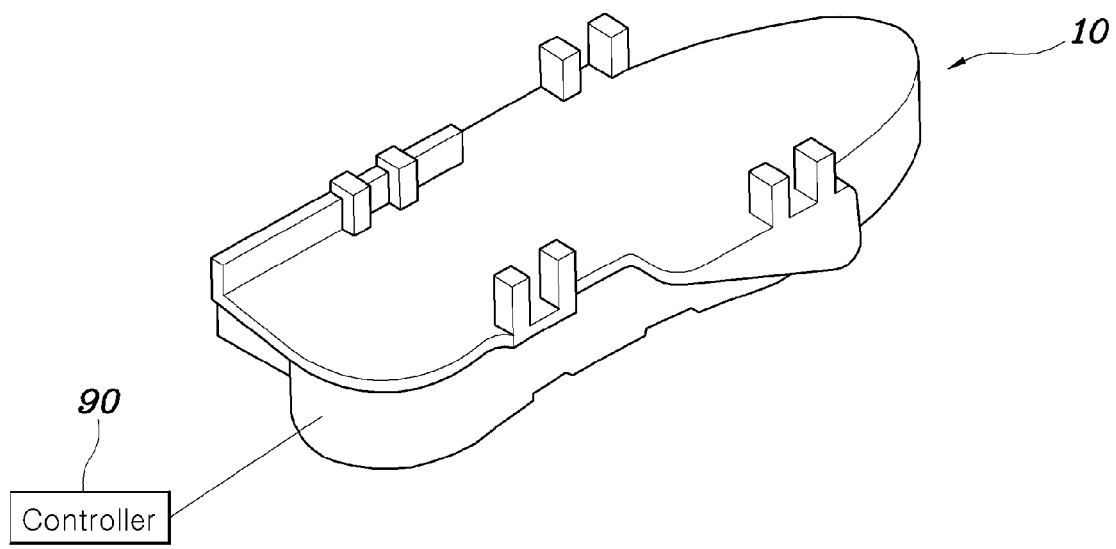
FIG. 1 is a view showing a robotic shoe of the related art.
Figure 2:
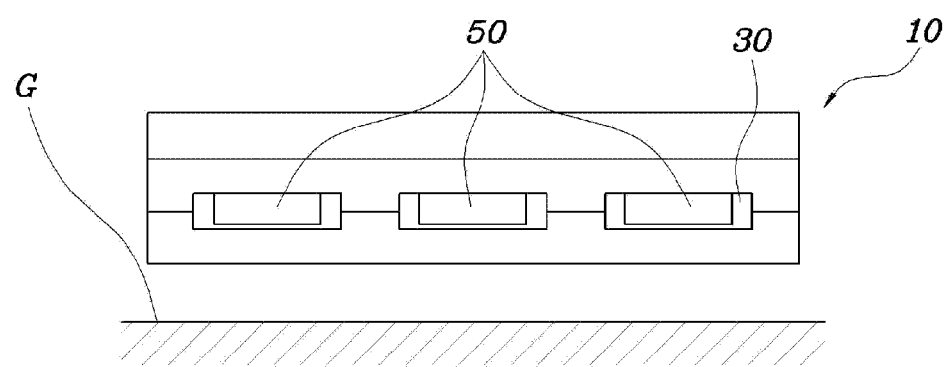
FIG. 2 shows a robotic shoe of the related art when the robotic shoe of the related art is not in contact with the ground.
Figure 3:
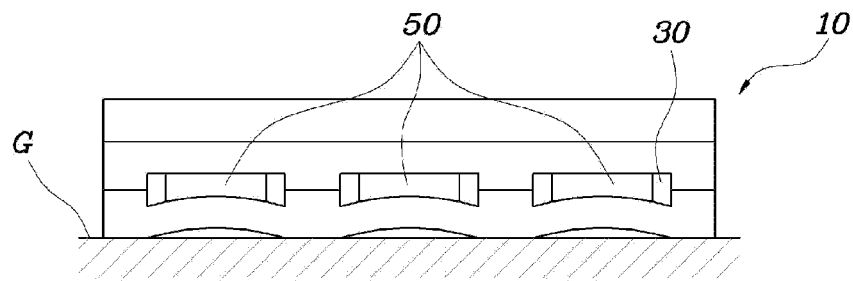
FIG. 3 shows a robotic shoe of the related art when the robotic shoe of the related art is in contact with the ground.

It should be understood that the appended drawings are not necessarily to scale, presenting a somewhat simplified representation of various features illustrative of the basic principles of the inventive concept. The specific design features of the present inventive concept as disclosed herein, including, for example, specific dimensions, orientations, locations, and shapes will be determined in part by a particular intended application and use environment.

In the figures, reference numbers refer to the same or equivalent parts of the present inventive concept throughout the several figures of the drawings.

DETAILED DESCRIPTION

Examples of the present inventive concept will be described below in more detail with reference to the accompanying drawings. The examples of the present inventive concept may, however, be embodied in different forms and should not be construed as limited to the examples set forth herein. Like reference numerals may refer to like elements throughout the specification.

A robotic shoe according to exemplary embodiments of the present inventive concept is described hereafter with reference to the accompanying drawings.

Figure 4:
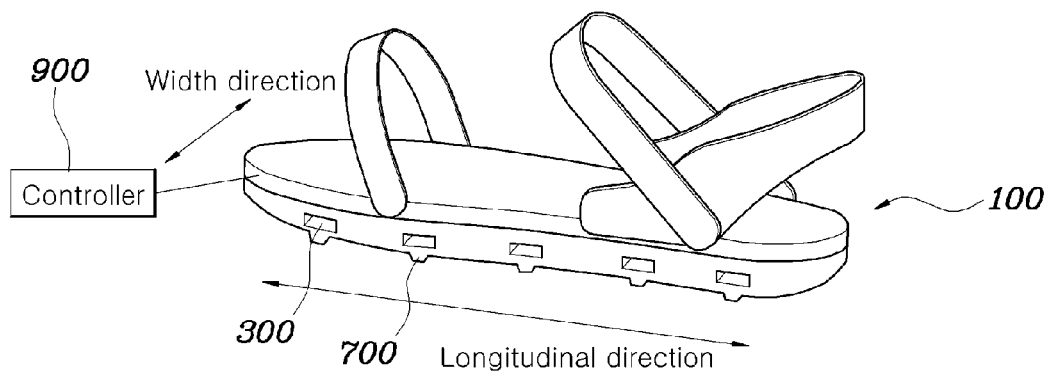
FIG. 4 is a view showing a robotic shoe according to an embodiment of the present inventive concept.

FIG. 4 is a view showing a robotic shoe according to embodiment of the present inventive concept. As shown in FIG. 4, the longitudinal direction and width direction are substantially perpendicular to each other in certain embodiments. The longitudinal direction is generally runs along the front to back direction of the robotic shoe, while the width direction runs from side to side of the robotic shoe. In certain embodiments, the longitudinal direction is longer than the width direction.

Figure 5:
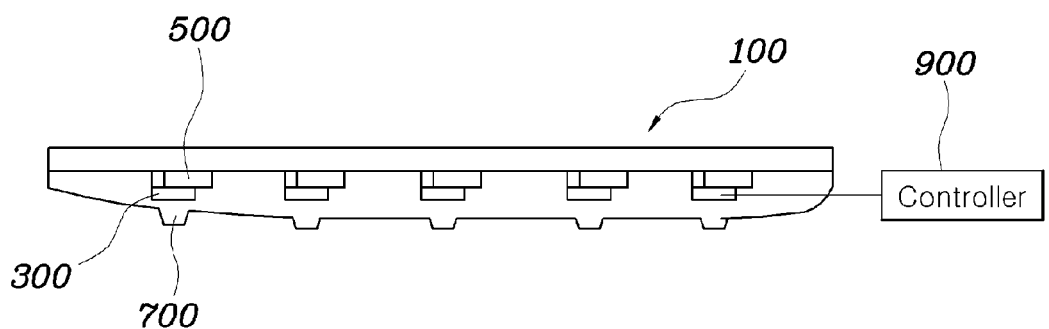
FIG. 5 is a side view of the sole shown in FIG. 4.
Figure 6:
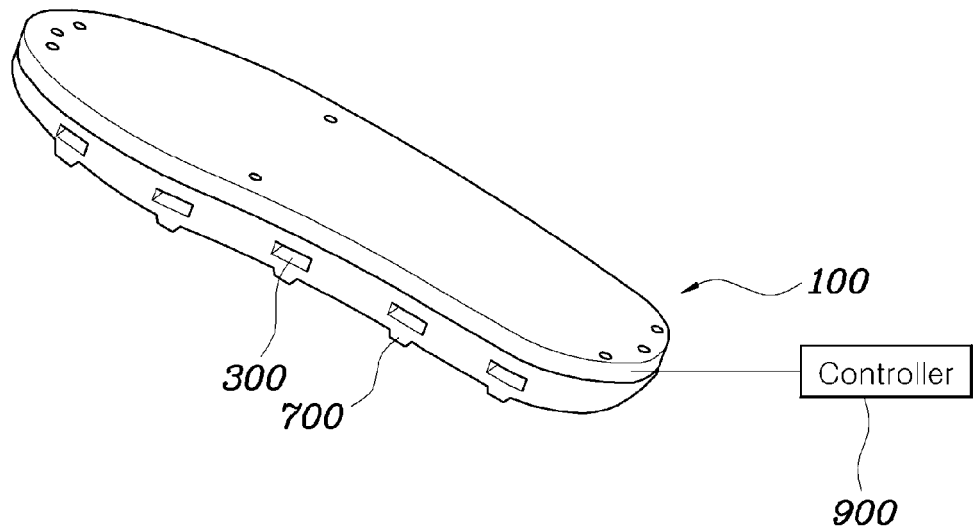
FIG. 6 is a perspective view of the sole shown in FIG. 4.
Figure 7:
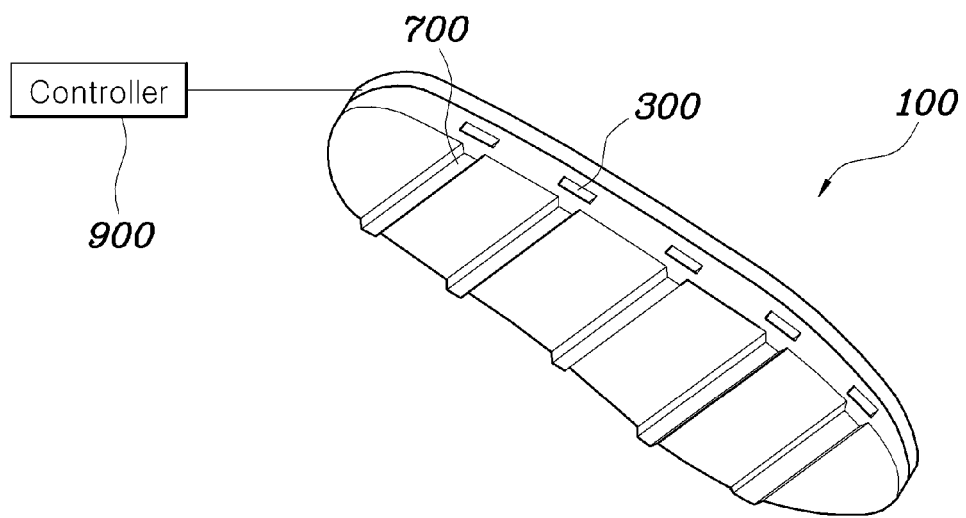
FIG. 7 is a perspective bottom view of the sole shown in FIG. 4.

FIG. 5 is a side view of the sole shown in FIG. 4. FIG. 6 is a perspective view of the sole shown in FIG. 4. FIG. 7 is a perspective bottom view of the sole shown in FIG. 4. The robotic shoe may include a robot sole 100 that can come in contact with the ground G, a plurality of mounting spaces 300 longitudinally spaced in the sole 100, optical sensors 500 (see FIG. 5) disposed in the mounting spaces 300, respectively, and projections 700 protruding from an underside of the sole 100. The projections 700 may come in contact with the ground G at the positions corresponding to the mounting spaces 300.

The mounting spaces 300 may be formed in along the width direction of the sole 100. The projections 700 corresponding to the mounting spaces 300 may be also formed in the width direction of the sole 100, as shown in FIG. 7. The portions of the sole 100 where the mounting spaces 300 are formed in the sole 100 may be made of an elastic material, particularly rubber. The optical sensor 50 may be non-contact type sensors.

Figure 8:
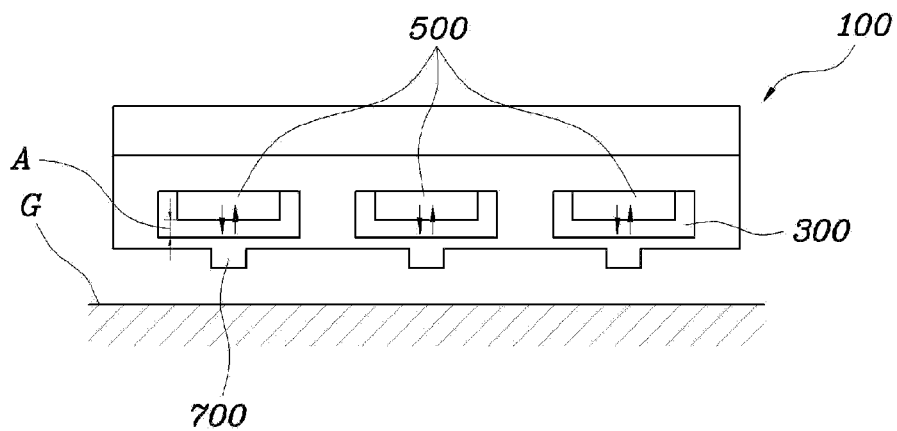
FIG. 8 is a view showing a robotic shoe according to an embodiment of the present inventive concept when the robotic shoe is not in contact with the ground.
Figure 9:
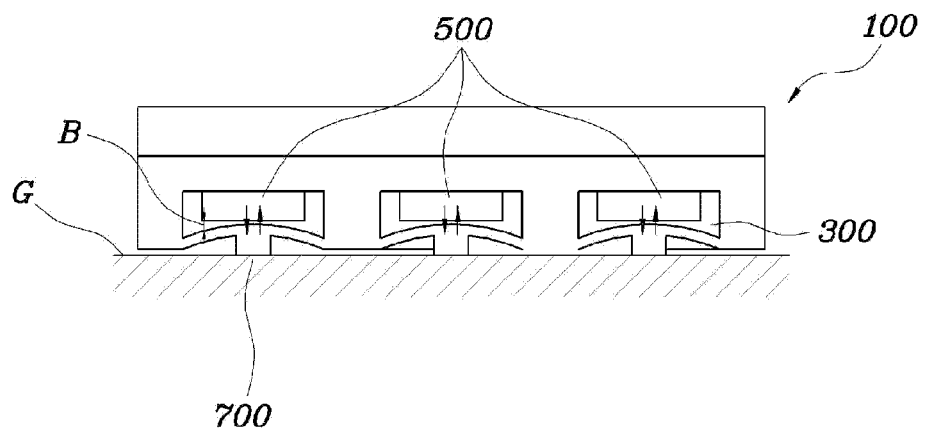
FIG. 9 is a view showing a robotic shoe according to an embodiment of the present inventive concept when the robotic shoe is in contact with the ground.

FIG. 8 is a view showing a robotic shoe according to an embodiment of the present inventive concept when the robotic shoe is not in contact with the ground. FIG. 9 is a view showing a robotic shoe according to an embodiment of the present inventive concept when the robotic shoe is in contact with the ground, and the sequence of operation of the robotic shoe will be described.

First, as shown in FIG. 8, mounting spaces 300 may be formed in the sole 100, and the optical sensors 500 may be disposed on the top portions of the mounting spaces 300, respectively. The top portions of the mounting spaces 300, are the portions or sides of the mounting spaces 300 that are the furthest portoin of the mounting spaces 300 from the ground G, when the robotic shoes are in use. A space with a predetermined length may be defined from an underside of the optical sensors 500 to a bottom portion of the mounting spaces 300. In certain embodiments of the disclosure, the bottom portion of the mounting spaces 300 oppose the top portions. The bottom portions of the mounting spaces 300 in certain embodiments are opposed to the top portions, and are the portions of the mounting spaces 300 that are closest to the ground when in use. A length between the underside of the optical sensors 500 and the bottom of the mounting spaces 300, as indicated by A in FIG. 8, may be set to 7~8 mm in an embodiment of the present inventive concept. Referring to FIG. 8, the projections 700 are not compressed, because the sole 100 is not in contact with the ground G.

The optical sensors 500 may sense a distance from the optical sensors 500 to the bottom portions of the mounting spaces 300 by radiating light downward from above, and then may operate when the sensed distance is equal to or less than a predetermined value. That is, the optical sensors 500 may set a distance threshold between an operation point and a return point, which may be set to 5 mm in the embodiment of the present inventive concept. Therefore, when the sole 100 does not come in contact with the ground G as shown in FIG. 8, the optical sensors 500 may not operate, because the length A stays at 7-8 mm with no change until the sole 100 comes in contact with the ground G.

Referring to FIG. 9, when the sole 100 is in contact with the ground G, the projections 700 may be compressed, thereby pushing up the underside of the sole 100, which is in contact with the ground G, into the mounting spaces 300. As the underside of the sole 100 is pushed up, a distance B between the optical sensors 500 and the underside of the sole 100 in the mounting spaces 300 is reduced when the sole 100 is in contact with the ground, so the optical sensors 500 may operate.

The optical sensors 500 may be given operation conditions when the distance is above or below a predetermined value, and may be set to be turned on or off depending on the operation conditions. The optical sensors 500 may be set to be turned on, when the distance between the underside of the optical sensors 500 and the bottom portion of the mounting spaces 300 reaches 5 mm or less, in the embodiment of the present inventive concept.

When the distance B has a value under 5 mm, for example 3~4 mm as shown in FIG. 9, the optical sensors 500 may be turned on and operate. A controller 900 may determine whether the robotic shoe moves forward or backward depending on whether the optical sensors 500 at the rear of the sole 100 operates first or the optical sensors 500 at the front operates first, on the basis of the order of sensed signals from the optical sensors 500. The controller 900 may comprehensively determine the intention of walking by determining a walk speed by comparing the operation speeds of the optical sensors 500. The controller 900 may be disposed in the sole 100 and not visible from outside, but is specifically shown in the figures of the drawings to help understanding the present inventive concept.

According to a robotic shoe of an embodiment of the present inventive concept, the robotic shoe can be used regardless of the load on the sole by operating the sensors when light is inputted, regardless of a reflective rate that is the limit condition of a non-contact type sensor with less influence by external light, by using non-contact type photosensors using modulated light instead of contact type sensors that are used in the related art, therefore the robotic shoe can resist considerable load while sensitively responding to an ever-changing environment and improve durability and reliability of sensors even under repetitive load.

Although an exemplary embodiment of the present inventive concept has been described for illustrative purposes, those skilled in the art will appreciate that various modifications, additions and substitutions are possible, without departing from the scope and spirit of the inventive concept as disclosed in the appended claims.

What is claimed is:

1. A robotic shoe, comprising:
   a robot sole having an underside capable of contacting the ground when in use;
   a plurality of mounting spaces longitudinally spaced-apart in the sole;
   a plurality of optical sensors disposed in respective ones of the mounting spaces,
   wherein the optical sensors are configured to sense distances from the optical sensors to bottoms of the mounting spaces and operate when a sensed distance value is equal to or less than a predetermined value; and
   projections protruding from the underside of the sole, which are capable of contacting the ground at positions corresponding to the mounting spaces when in use.

2. The robot shoe of claim 1, wherein the mounting spaces extend along a width direction of the sole.

3. The robotic shoe of claim 1, wherein the optical sensors are disposed on tops of the mounting spaces and configured to radiate light downward from above.

4. The robotic shoe of claim 1, further comprising a controller configured to determine an intention of walking on the basis of the order of sensed signals of the optical sensors.

5. The robotic shoe of claim 1, wherein the optical sensors are non-contact type photosensors.

6. The robotic shoe of claim 1, wherein when the projections come in contact with the ground, bottom portions of the mounting spaces are pushed into the mounting space and a distance between the optical sensors and the bottom portions of the mounting spaces is decreased.

7. The robotic shoe of claim 1, wherein portions of the sole where the mounting spaces are formed in the sole are made of an elastic material.

* * * * *